US009451925B2

(12) United States Patent
Furuta et al.

(10) Patent No.: US 9,451,925 B2
(45) Date of Patent: Sep. 27, 2016

(54) NUCLEAR MEDICINE DIAGNOSIS APPARATUS

(71) Applicant: Shimadzu Corporation, Kyoto (JP)

(72) Inventors: Masafumi Furuta, Kyoto (JP); Junichi Ohi, Kyoto (JP); Masakuni Tachi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/025,674

(22) PCT Filed: Aug. 29, 2014

(86) PCT No.: PCT/JP2014/072818
§ 371 (c)(1),
(2) Date: Mar. 29, 2016

(87) PCT Pub. No.: WO2015/049943
PCT Pub. Date: Apr. 9, 2015

(65) Prior Publication Data
US 2016/0213342 A1 Jul. 28, 2016

(30) Foreign Application Priority Data
Oct. 1, 2013 (JP) .................................. 2013-206617

(51) Int. Cl.
*A61B 6/03* (2006.01)
*A61B 6/04* (2006.01)
*A61B 6/00* (2006.01)

(52) U.S. Cl.
CPC ............... *A61B 6/502* (2013.01); *A61B 6/037* (2013.01); *A61B 6/0435* (2013.01); *A61B 6/4275* (2013.01)

(58) Field of Classification Search
CPC .. A61B 6/037; A61B 6/0435; A61B 6/4275; A61B 6/502
See application file for complete search history.

(56) References Cited

U.S. PATENT DOCUMENTS

2010/0074399 A1* 3/2010 Majewski ................. G01T 1/00
378/37
2014/0128729 A1 5/2014 Furuta

FOREIGN PATENT DOCUMENTS

WO 2013014715 A1 1/2013

OTHER PUBLICATIONS

International Search Report dated Dec. 2, 2014 from corresponding International Application No. PCT/JP2014/072818; 8 pgs.

* cited by examiner

*Primary Examiner* — Mark R Gaworecki
(74) *Attorney, Agent, or Firm* — Maier & Maier, PLLC (57) ABSTRACT

With a mammography PET apparatus, a supporting face includes a detector ring region, and a detector-outside region as an outside area of the detector ring region. The detector ring region is higher than the detector-outside region. An elastic lower-layer mat is disposed on the detector-outside region. An upper-layer mat, softer than the lower-layer mat, is disposed on the detector ring region and the lower-layer mat across a boundary between the detector ring region and the lower-layer mat. Accordingly, an edge of the lower-layer mat harder than the upper-layer mat is covered with the upper-layer mat, leading to alleviation of pain to a subject M caused by the edge of the lower-layer mat.

5 Claims, 10 Drawing Sheets

NUCLEAR MEDICINE DIAGNOSIS APPARATUS

RELATED APPLICATIONS

This application is the U.S. National Phase application under 35 U.S.C. §371, of international Application No. PCT/JP2014/072818 filed on Aug. 29, 2014, which in turn claims the benefit of Japanese application No. 2013-206617, filed on Oct. 1, 2013 the disclosures of which Applications are incorporated by reference herein.

TECHNICAL FIELD

The present invention relates to a nuclear medicine diagnosis apparatus that measures radiation (e.g., γ-rays) generated from a subject to which radiopharmaceutical is administered.

BACKGROUND ART

Examples of currently-used nuclear medicine diagnosis apparatus of this type, i.e., an ECT (Emission Computed Tomography) apparatus, include a PET (Positron Emission Tomography) apparatus. The PET apparatus reconstructs a tomographic image of a subject only when a plurality of detectors simultaneously detects two gamma-rays generated through annihilation of a positive electron (Positron). Specifically, radiopharmaceutical containing positron-emitting radionuclide is administered to the subject. Then paired annihilation gamma-rays of 511 Key emitted from the administered subject are detected with the detectors each formed by many detector elements (e.g., scintillators). Thereafter, when two gamma-rays are detected with two of the detectors within a certain time period, the gamma-rays are detected "coincidently". Moreover, a position where the paired annihilation gamma-rays are generated is identified to be on a line connecting the two detectors. Then information on such coincidence is stored for reconstruction to obtain a positron-emitting radionuclide image, i.e., a tomographic image.

The PET apparatus includes a plurality of detectors disposed in a ring shape so as to surround the subject for enhanced detection sensitivity. Such arrangement that the detectors are disposed in a ring shape is referred to as a detector ring. In addition, with a site-specific PET apparatus that captures a part of the subject, detectors are disposed closely to the subject so as to surround only the part of the subject. This achieves more enhanced detection sensitivity.

Figure 11:
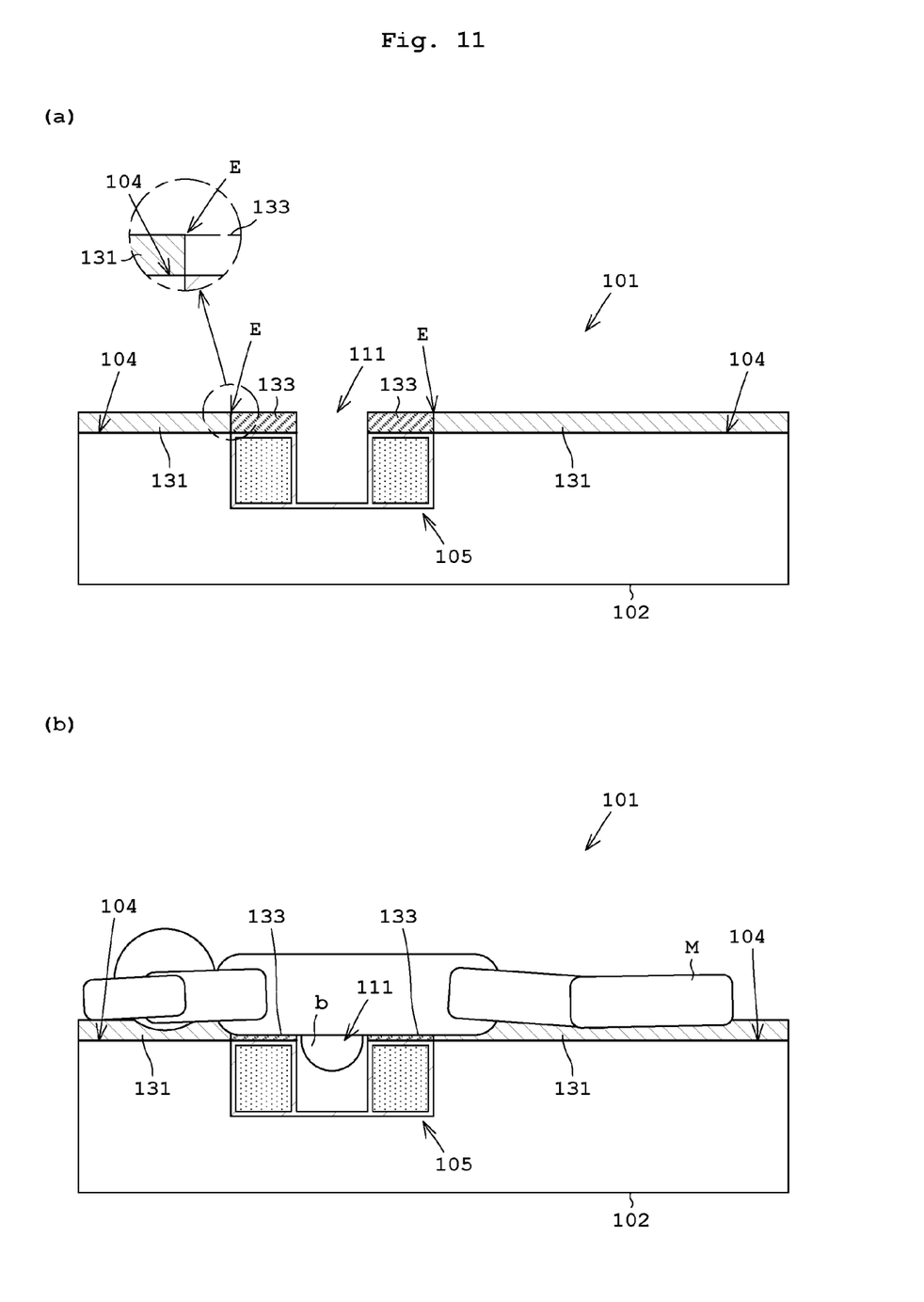
FIG. 11(a) is a vertical sectional view of a currently-used mammography PET apparatus.
FIG. 11(b) illustrates the mammography PET apparatus of FIG. 11 (a) with a subject placed therein.

Examples of the site-specific PET apparatus include a mammography PET apparatus. See Patent Literature 1. FIGS. 11(a) and 11(b) each illustrate a vertical sectional view of a currently-used mammography PET apparatus 101 (Patent Literature 1). The mammography PET apparatus 101 includes a supporting unit 102 that supports a subject M in a prone position or in a seated position, an opening 111 formed on a supporting face 104 of the supporting unit 102, and a detector ring 105 that is disposed below the supporting face 104 of the supporting unit 102 and surrounds a breast b of the subject M inserted into opening 111.

The mammography PET apparatus 101 of Patent Literature 1 has the following drawback. That is, breast cancer mostly occurs at a root of the breast b of the subject M, i.e., around a chest wall of the subject M. Accordingly, the breast b of the subject M is desired to be inserted more deeply into a field of view of the detector ring 105. On the other hand, a single mat is disposed on the supporting face 104 as a cushion. This mat prevents more deep insertion of the breast b of the subject M into the field of view. As a result, a chest of the subject M should be pressed toward the detector ring 105 with an own force of the subject M using a handle.

Moreover, when no mat is disposed, the subject M contacts directly to the hard supporting face 104. Accordingly, significant pain induces on sternum of the subject M or a site of the subject M contacting to an outer edge of the opening 111, for example.

Consequently, Patent Literature 1 has suggested the following. Specifically, as illustrated in FIGS. 11(a) and 11(b), the mammography PET apparatus 101 includes a chest mat 133 disposed around the opening 111 in the supporting unit 102 for supporting the chest of the subject M, and an outer mat 131 formed outward of the chest mat 133 for supporting the subject M. That is, two types of mats 131 and 133 are disposed side by side for different sites. The chest mat 133 is formed of a material softer (having a greater sinking ratio) than the outer mat 131. Upon support of the subject M with the chest mat 133 and the outer mat 131, the chest mat 133 sinks more deeply than the outer mat 131. As a result, a weight of the subject M concentrates at the chest of the subject M, i.e., around the breast b. This facilitates pressing of the chest of the subject M against the detector ring 105. In addition, since the chest mat 133 supports the subject M, pain induced on the subject M is alleviated.

PATENT LITERATURE

Patent Literature 1: International Patent Publication WO 2013/014715

SUMMARY OF INVENTION

Technical Problem

However, subsequent study reveals that, in Patent Literature 1, when the chest mat 133 contacts to the bottom due to the weight of the subject M, an edge E (corner) of the outer mat 131 arranged side by side to the chest mat 133 contacts to subject M, leading to possible pain to the subject M. Consequently, it is desired to alleviate the pain to the subject M caused by the edge E of the outer mat 131 harder than the chest mat 133.

The present invention has been made regarding the state of the art noted above, and its one object is to provide a nuclear medicine diagnosis apparatus that alleviates pain to a subject caused by insertion of a capturing site of the subject into a detector ring.

The present invention is constituted as stated below to achieve the above object. A first aspect of the present invention provides a nuclear medicine diagnosis apparatus. The nuclear medicine diagnosis apparatus includes a supporting unit that supports a subject, an opening formed on a supporting face of the supporting unit into which a capturing target site as a projection part of the subject is inserted, and a detector ring opposite to the subject across the supporting face of the supporting unit and including a plurality of detectors in ring-shape arrangement for detecting radiation emitted from the capturing target site inserted into the opening. The supporting face includes a detector ring region corresponding to the arrangement of the detector ring, and a detector-outside region as an outside area of the detector ring region. The detector ring region is higher than the detector-outside region. An elastic lower-layer mat is disposed on the detector-outside region, and an upper-layer mat softer than the lower-layer mat is disposed on the detector ring region and the lower-layer mat across a boundary between the detector ring region and the lower-layer mat.

With the nuclear medicine diagnosis apparatus according to the first aspect of the present invention, the supporting face includes the detector ring region corresponding to the arrangement of the detector ring, and the detector-outside region as the outside area of the detector ring region. The detector ring region is higher than the detector-outside region. Moreover, the elastic lower-layer mat is disposed on the detector-outside region. The upper-layer mat, softer than the lower-layer mat, is disposed on the detector ring region and the lower-layer mat across the boundary between the detector ring region and the lower-layer mat. Accordingly, an edge of the lower-layer mat harder than the upper-layer mat is covered with the upper-layer mat, leading to alleviation of pain to the subject caused by the edge of the lower-layer mat.

Moreover, the lower-layer mat harder than the upper-layer mat is disposed on the detector-outside region that is lower than the detector ring region. Accordingly, this compensates a step portion between the detector ring region and the detector-outside region. In addition, the lower-layer mat is harder than the upper-layer mat and thus is unlikely to sink. As a result, this obtains alleviation of pain caused by contact of the subject to the edge of the detector ring region. Moreover, if the lower-layer mat is soft and sinks deeply, the edge of the detector ring region in the step portion between the detector ring region and the detector-outside region induces pain to the subject.

Moreover, when no step portion is present between the detector ring region and the detector-outside region, and thus the detector ring region is flush with the detector-outside region, a protrusion part of the subject, other than the capturing target site, prevents the subject from being pressed around the opening of the detector ring region. In addition, load is concentrated on the protrusion part, leading to induction of pain to the subject. The detector ring region is higher than the detector-outside region, and the lower-layer mat is disposed on the detector-outside region. Consequently, the protrusion part can be disposed at a position lower than the detector ring region, and is held with the lower-layer mat. This facilitates pressing of the subject around the opening while pain to the subject is alleviated.

Moreover, since the upper-layer mat is softer than the lower-layer mat, the upper-layer mat is able to be compressed thinly around the opening of the detector ring region. This allows deep insertion of the capturing target site as the projection part of the subject into the field of view of the detector ring.

Moreover, it is preferred in the nuclear medicine diagnosis apparatus according to the first aspect of the present invention that the detector-outside region is divided into a head region corresponding to the head of the subject, and a head-outside region other than the head region. The lower-layer mat is disposed on the head-outside region. A head mat softer than the lower-layer mat is disposed on the head region.

For instance, it is assumed that the supporting unit supports the subject from a front side while the lower-layer and the upper-layer mat are disposed between the supporting unit and the subject, and the breast is the capturing target site of the subject. In such a case, the head of subject structurally projects forward from the chest wall, load is likely to be applied to the head when the subject is pressed around the opening, i.e., toward the detector ring. Consequently, the head causes prevention of the pressing. Accordingly, in the present invention, the head mat softer than the lower-layer mat is disposed so as for the head of the subject to sink deeply in the head mat than the lower-layer mat, achieving prevention of the pressing.

Moreover, one embodiment of the nuclear medicine diagnosis apparatus according to the first aspect of the present invention is configured such that the detector ring region is equal in level to a top face of the lower-layer mat. This allows the minimum step portion between the detector ring region and the detector-outside region, leading to alleviated pain to the subject caused by the edge of the detector ring region in the step portion between the detector ring region and the detector-outside region.

Moreover, another embodiment of the nuclear medicine diagnosis apparatus according to the first aspect of the present invention is configured such that the detector ring region is higher than a top face of the lower-layer mat toward the subject. This facilitates application of the weight of the subject to the detector ring, leading to more effective insertion of the capturing target site into the field of view.

Another embodiment of the nuclear medicine diagnosis apparatus according to the first aspect of the present invention is configured such that a top face of the lower-layer mat is higher than the detector ring region toward the subject. In other words, the detector ring region is lower than the top face of the lower-layer mat. For instance, when the breast is the capturing target site of the subject, torso of the subject warps and the breast stretches naturally. This allows more effective insertion of the capturing target site into the field of view.

Advantageous Effects of Invention

With the nuclear medicine diagnosis apparatus according to the present invention, the supporting face includes the detector ring region corresponding to the arrangement of the detector ring, and the detector-outside region as the outside area of the detector ring region. The detector ring region is higher than the detector-outside region. Moreover, the elastic lower-layer mat is disposed on the detector-outside region. The upper-layer mat, softer than the lower-layer mat, is disposed on the detector ring region and the lower-layer mat across the boundary between the detector ring region and the lower-layer mat. Accordingly, an edge of the lower-layer mat harder than the upper-layer mat is covered with the upper-layer mat, leading to alleviation of pain to the subject caused by the edge of the lower-layer mat.

BRIEF DESCRIPTION OF DRAWINGS

FIGS. 10 (a) to (c) are each a plan view of an opening according to the modification.

PREFERRED EMBODIMENT 1

Figure 1:
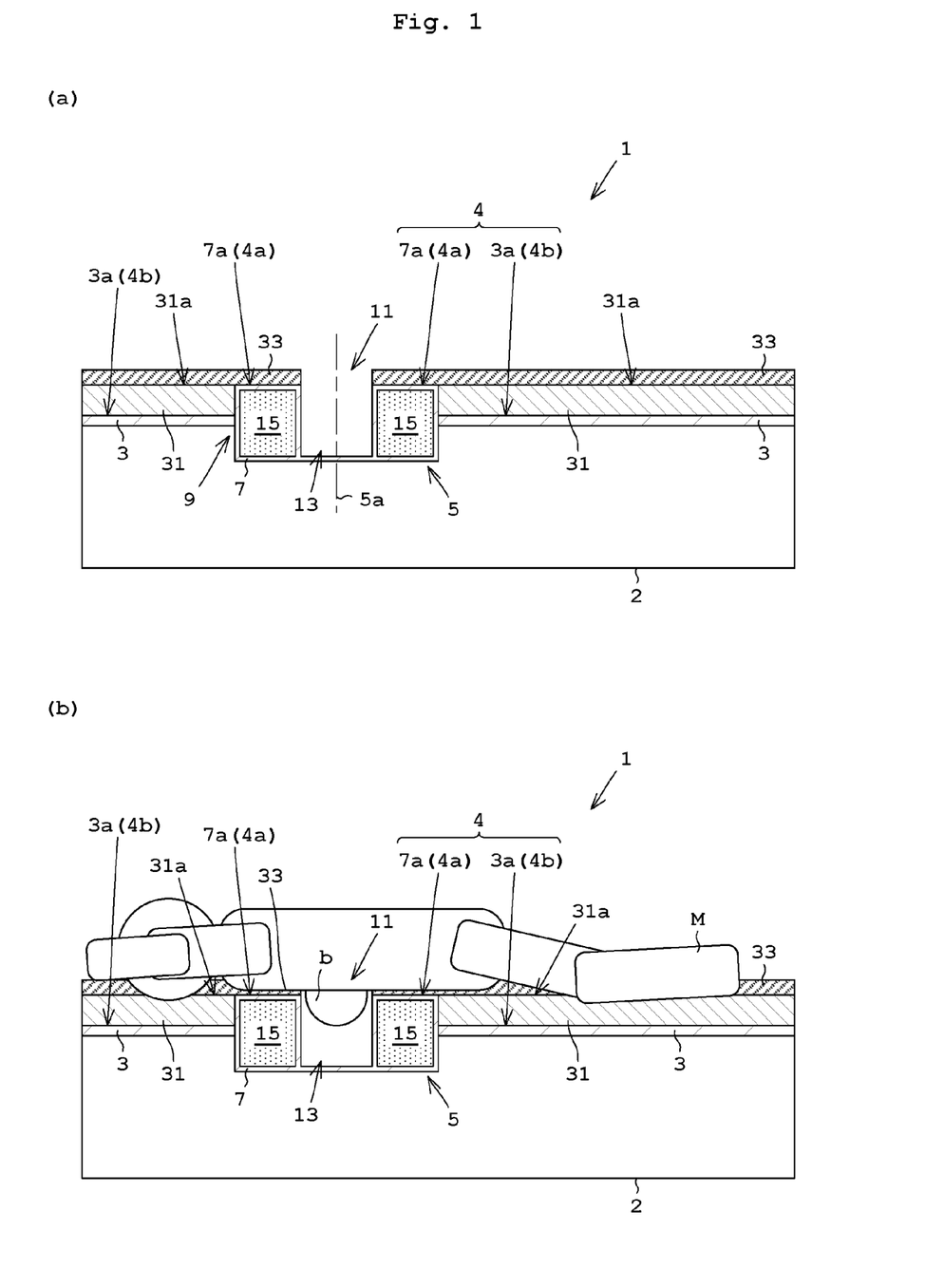
FIG. 1(a) is a vertical sectional view of a mammography PET apparatus according to Preferred Embodiment 1.
FIG. 1(b) illustrates the mammography PET apparatus of FIG. 1(a) with a subject placed therein.

The following describes Preferred Embodiment 1 of the present invention with reference to drawings. The present embodiment describes a mammography PET apparatus that captures the breast of a subject for a capturing target site as one example of a nuclear medicine diagnosis apparatus. FIG. 1(a) is a vertical sectional view of the mammography PET apparatus according to Embodiment 1, and FIG. 1(b) illustrates the mammography PET apparatus of FIG. 1(a) with the subject placed therein.

Reference is made to FIGS. 1(a) and 1(b). A mammography PET apparatus 1 includes a supporting unit 2 (also referred to as a gantry) that supports a subject M from a front side thereof. The supporting unit 2 includes a top board 3 on which the subject M is held. The top board 3 includes a top board supporting face 3a adjacent to the subject M. The supporting unit 2 includes a supporting face 4 having the top board supporting face 3a and a case supporting face 7a, which is to be mentioned later. As illustrated in FIG. 1(b), the subject M is placed on the supporting unit 2 in a prone position.

The supporting unit 2 includes a detector ring 5, and a case 7 that accommodates the detector ring 5. Specifically, the top board 3 includes a hole 9 in which the detector ring 5 and the case 7 are disposed. The case 7 includes a case supporting face 7a adjacent to the subject M. Here, the top board supporting face 3a and the case supporting face 7a are disposed in parallel, and the top board supporting face 3a and the case supporting face 7a (i.e., the supporting face 4) are disposed horizontally. Moreover, the case 7 is made of metal.

An opening 11 is disposed in the case supporting face 7a of the case 7 provided in the supporting unit 2 for inserting the breast b of the subject M. The opening 11 is provided with a recessed accommodating unit 13 that accommodates the breast b of the subject M. The accommodating unit 13 is formed along a contour of the case 7.

The detector ring 5 is disposed opposite to the subject M across the case supporting face 7a. The detector ring 5 includes a plurality of γ-ray detectors 15 arranged in a ring shape about an axis 5a within the accommodating unit 13, the axis 5a being perpendicular with respect to the top board supporting face 3a. See FIG. 2. That is, the detector ring 5 detects γ-rays generated from the breast b of the subject M inserted into the opening 11 using the γ-ray detectors 15 arranged in the ring shape. The γ-ray detectors 15 correspond to the detector in the present invention.

The γ-ray detectors 15 each include scintillator blocks, a light guide, and a photomultiplier (each not shown). The scintillator blocks are plural and are arranged two-dimensionally. When the γ-rays generated from the breast b of the subject M scintillator block enter into the scintillator blocks, the scintillator blocks convert the γ-rays into light. The converted light is transmitted via the light guide to the photomultiplier. The photomultiplier converts the light into electric signals, and outputs the signals. For instance, a DOI (depth of interaction) detector that includes multi-layered scintillator blocks and obtains positional information in a depth direction is used as the γ-ray detector 15.

Figure 2:
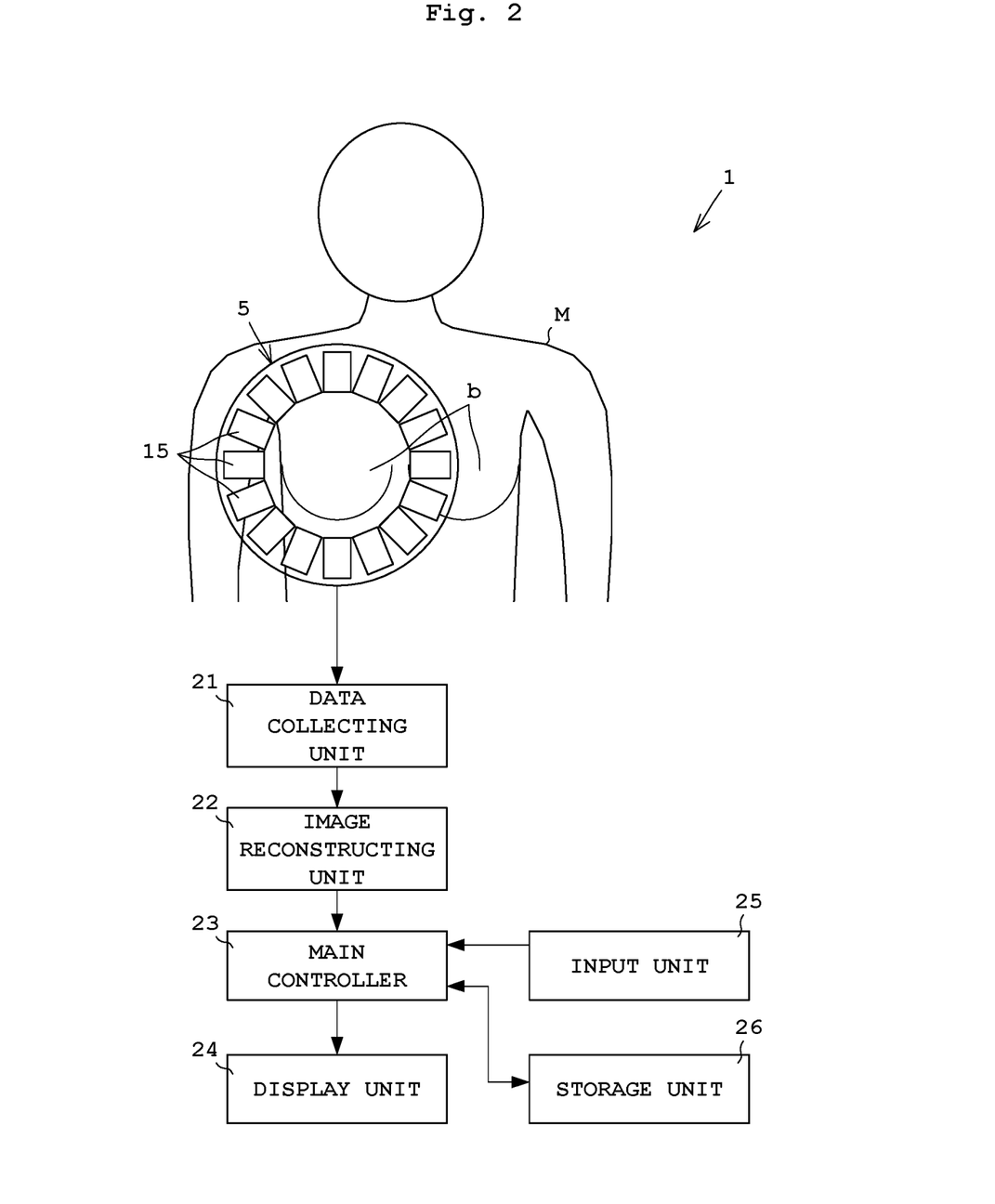
FIG. 2 is a block diagram of the mammography PET apparatus according to the Preferred Embodiment 1.

FIG. 2 is a block diagram of the mammography PET apparatus according to Embodiment 1. The detector ring 5 (γ-ray detectors 15) is connected to a data collecting unit 21. The data collecting unit 21 collects an event as coincident information, the event being only when two γ-ray detectors 15 detect paired γ-rays in a certain time period in accordance with electric signals outputted from the γ-ray detectors 15. The collected coincident information is stored in a collecting memory, not shown. An image reconstructing unit 22 performs image reconstruction to the collected coincident information to generate a tomographic image (positron-emitting radionuclide distribution image).

Moreover, the mammography PET apparatus 1 further includes a main controller 23 that controls en bloc each units of the apparatus 1, a display unit 24 that displays the tomographic image generated by the image reconstructing unit 22, an input unit 25 used for operator's input setting or operation, and a storage unit 26 that stores the tomographic image generated by the image reconstructing unit 22. The main controller 23 includes a central processing unit (CPU). The display unit 24 includes a monitor. The input unit 25 includes a keyboard, and a mouse. The storage unit 26 includes a storage medium such as a ROM (Read-only Memory), a RAM (Random-Access Memory), and a hard disk.

<Lower-Layer Mat and Upper-Layer Mat>

The following describes a lower-layer mat 31 and an upper-layer mat 33 between the subject M and the supporting face 4, which is the feature of the present invention.

Figure 3:
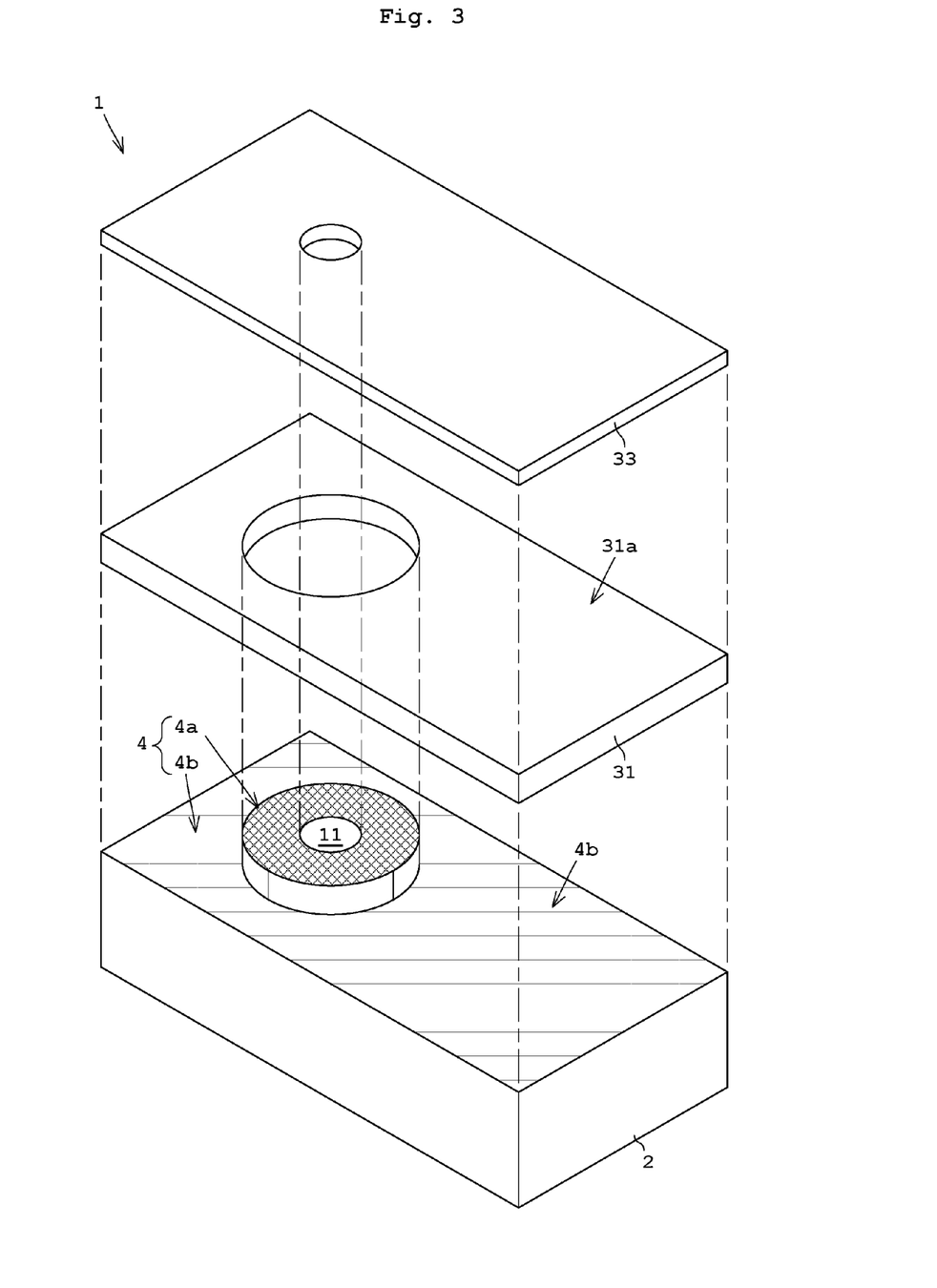
FIG. 3 is an exploded perspective view of the mammography PET apparatus according to the Preferred Embodiment 1.

FIG. 3 is an exploded perspective view of the mammography PET apparatus according to Embodiment 1. Firstly, the supporting face 4 of the supporting unit 2 includes a detector ring region 4a, corresponding to arrangement of the detector ring 5, and a detector-outside region 4b as an outside area of the detector ring region 4a. That is, the detector ring region 4a corresponds to the case supporting face 7a, and the detector-outside region 4b corresponds to the top board supporting face 3a. Here, the region corresponding to the arrangement of the detector ring 5 is any region outwardly larger than the contour of the detector ring 5.

A step portion is provided between the detector ring region 4a and the detector-outside region 4b. The detector ring region 4a is higher than the detector-outside region 4b toward the subject M (i.e., upwardly). On the other hand, the detector-outside region 4b is lower than the detector ring region 4a. The lower-layer mat 31 is disposed on the detector-outside region 4b so as to compensate the step portion for mainly supporting the subject M. The lower-layer mat 31 has elasticity as a cushion.

Moreover, as illustrated in FIG. 1(a), there is no step portion between a top face 31a of the lower-layer mat 31 and the detector ring region 4a of the supporting face 4, and thus a boundary therebetween is planar. In other words, the detector ring region 4a has the same level as the top face 31a of the lower-layer mat 31. This achieves the minimum step portion between the detector ring region 4a and the detector-outside region 4b, leading to alleviated pain to the subject M caused by an edge of the detector ring region 4a in the step portion between the detector ring region 4a and the detector-outside region 4b.

The lower-layer mat 31 is formed by a sponge of urethane and the like. It is desirable that the lower-layer mat 31 is formed by a material of non-low repulsion type. The sponge of low repulsion type may unexpectedly sink, for example, may float under a weight load. Examples of the sponge of non-low repulsion type include a sponge of high elasticity type (with an impact resilience of more than 50%), and a sponge not corresponding to a low repulsion type (with an impact resilience of less than 15%) and to the high elasticity type in accordance with Japanese Industrial Standards (JIS) (K6401). The lower-layer mat 31 harder than the upper-layer mat 33, to be mentioned later, is used.

The upper-layer mat 33, softer than the lower-layer mat 31, is provided on the detector ring region 4a and the lower-layer mat 31 so as to be disposed across the boundary between the detector ring region 4 and the lower-layer mat 31. The upper-layer mat 33 is formed by a sponge of urethane and the like in the same manner as the lower-layer mat 31, and thus formed by a material of non-low repulsion type. Here, the upper-layer mat 33 may be integrally formed at the boundary between the detector ring region 4 and the lower-layer mat 31. Alternatively, the upper-layer mat 33 may be separated as long as the detector ring region 4 and the lower-layer mat 31 are arranged in series. Moreover, the upper-layer mat 33 may not be provided to the outer edge of the lower-layer mat 31 as long as the upper-layer mat 33 is disposed across the boundary between the detector ring region 4 and the lower-layer mat 31.

<Operation of Mammography PET Apparatus>

The following describes operation of the mammography PET apparatus 1 according to Embodiment 1. Reference is made to FIG. 1(a). The subject M is placed on the supporting unit 2 (i.e., on the upper-layer mat 33). As illustrated in FIG. 1(b), the subject M is placed in a prone position while the breast b thereof is inserted into the opening 11. When the subject M is placed on, the weight of the subject M causes the lower-layer mat 31 and the upper-layer mat 33 to sink.

The supporting face 4 is hard, and the detector ring region 4a is higher than the detector-outside region 4b toward the subject M. This facilitates pressing around the breast b of the subject M. Moreover, the lower-layer mat 31 is disposed on the detector-outside region 4b around the detector ring region 4a. The lower-layer mat 31 supports the subject M not with the hard supporting face 4 but with an elastic material. Consequently, pain caused by contact to the hard supporting face 4 is alleviated. Moreover, the lower-layer mat 31 is formed by a material harder than the upper-layer mat 33. Consequently, this prevents excessive sinking of the subject M. As a result, the subject M contacts to the edge of the detector ring region 4a in the step portion between the detector ring region 4a and the detector-outside region 4b, leading to alleviation of pain to the subject M.

Moreover, the upper-layer mat 33 softer than the lower-layer mat 31 is disposed on the detector ring region 4a and the lower-layer mat 31. The weight of the subject M also causes the upper-layer mat 33 to sink. Since the upper-layer mat 33 is formed by the material softer than the lower-layer mat 31, the upper-layer mat 33 on the detector ring region 4a is compressed thinly. As a result, the upper-layer mat 33 acts together with the higher detector ring region 4a, allowing effective pressing of the chest of the subject M against the detector ring region 4a. This achieves deeper insertion of the breast b of the subject M into the field of view in the opening 11.

Moreover, the chest of the subject M contacts to the detector ring region 4a via the upper-layer mat 33. This allows alleviation of pain caused by contact to the hard supporting face 4. In Patent Literature 1 (see FIG. 11(a)), two types of mats 131 and 133 are arranged side by side, and contact of the subject M to the edge E of the harder mat 131 induces pain to the subject M. In contrast to this, the upper-layer mat 33 covers the edge of the lower-layer mat 31 formed by the material harder than the upper-layer mat 33. This allows alleviation of pain to the subject M caused by contact to the edge of the lower-layer mat 31.

When the subject M is placed on the supporting unit 2, the breast b of the subject M is inserted more deeply into the field of view of the detector ring 5. Under such a condition, capturing (measuring) is performed. Radiopharmaceutical is administered in advance to the subject M. Accordingly, γ-rays are generated from the breast b of the subject M. The generated paired γ-rays are emitted at a straight angle opposite to each other. The γ-ray detectors 15 of the detector ring 5 detect paired γ-rays. The data collecting unit 21 collects an event that two γ-ray detectors 15 detected paired γ-rays for a certain time period as coincident information. The image reconstructing unit 22 reconstructs the collected coefficient information to generate a tomographic image. The generated tomographic image is displayed on the display unit 24, and is stored in the storage unit 26.

With the present embodiment, the supporting face 4 includes the detector ring region 4a corresponding to the arrangement of the detector ring 5, and the detector-outside region 4b as the outside region of the detector ring region 4a. The detector ring region 4a is higher than the detector-outside region 4b. Moreover, the elastic lower-layer mat 31 is disposed on the detector-outside region 4b, and the upper-layer mat 33, softer than the lower-layer mat 31, is disposed on the detector ring region 4a and the lower-layer mat 31 across the boundary between the detector ring region 4a and the lower-layer mat 31. Accordingly, an edge of the lower-layer mat 31 harder than the upper-layer mat 33 is covered with the upper-layer mat 33, leading to alleviation of pain to the subject M caused by the edge of the lower-layer mat 31.

Moreover, the lower-layer mat 31 harder than the upper-layer mat 33 is disposed on the detector-outside region 4b lower than the detector ring region 4a. Accordingly, this compensates the step portion between the detector ring region 4a and the detector-outside region 4b. In addition, the lower-layer mat 31 is harder than the upper-layer mat 33 and thus is unlikely to sink. As a result, this obtains alleviation of pain caused by contact of the subject M to the edge of the detector ring region 4 in the step portion. Moreover, if the lower-layer mat 31 is soft and sinks deeply, the edge of the detector ring region 4a in the step portion between the detector ring region 4a and the detector-outside region 4b induces pain on the subject M.

Moreover, when no step portion is present between the detector ring region 4a and the detector-outside region 4b, and thus the detector ring region 4a is flush with the detector-outside region 4b, a protrusion part of the subject M (e.g., head or shoulders), other than the breast b of the subject M, prevents the subject M from being pressed around the opening 11 of the detector ring region 4a. In addition, load is concentrated on the protrusion part, leading to induction of pain on the subject M. The detector ring region 4a is higher than the detector-outside region 4b, and the lower-layer mat 31 is disposed on the detector-outside region 4b. Consequently, the protrusion part is able to be disposed at a position lower than the detector ring region 4a, and is held with the lower-layer mat 31. This facilitates pressing of the subject M around the opening 11 while pain to the subject is alleviated.

Moreover, since the upper-layer mat 33 is softer than the lower-layer mat 31, the upper-layer mat 33 is able to be compressed thinly around the opening 11 of the detector ring region 4a. This allows deeper insertion of the breast B of the subject M into the field of view of the detector ring 5.

PREFERRED EMBODIMENT 2

Figure 4:
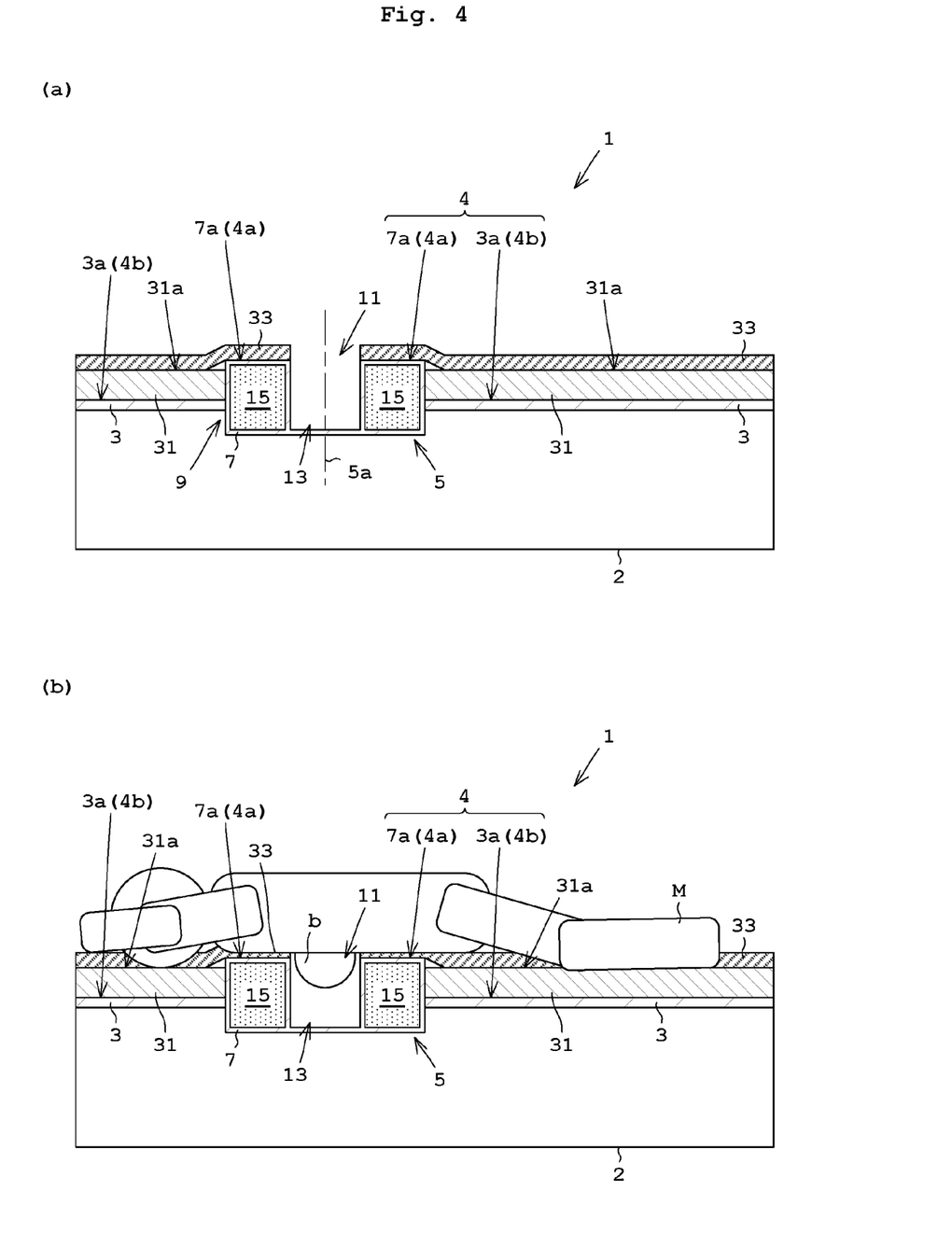
FIG. 4(a) is a vertical sectional view of a mammography PET apparatus according to Preferred Embodiment 2.
FIG. 4(b) illustrates the mammography PET apparatus of FIG. 4(a) with a subject placed therein.

The following describes Preferred Embodiment 2 of the present invention with reference to drawings. Here, description of the configuration common to that of Embodiment 1 is to be omitted. FIG. 4(a) is a vertical sectional view of a mammography PET apparatus according to the Embodiment 2, and FIG. 4(b) illustrates the mammography PET apparatus of FIG. 4(a) with a subject placed therein.

The Embodiment 1 mentioned above describes the relationship between the detector ring region 4a and the top face 31a of the lower-layer mat 31 such that the detector ring region 4a is equal in level to the top face 31a of the lower-layer mat 31. In contrast to this, as illustrated in FIGS. 4(a) and 4(b) of the present embodiment, the detector ring region 4a is higher than the top face 31a of the lower-layer mat 31 toward the subject M.

With the present embodiment, the weight of the subject M is readily applied to the detector ring 5, achieving more effective insertion of the breast b of the subject M into the field of view.

Moreover, in the present embodiment, the detector ring region 4a is higher than the top face 31a of the lower-layer mat 31 toward the subject M. The higher detector ring region 4a causes a larger influence of the edge of the detector ring region 4a in the step portion of the detector ring region 4a and the detector-outside region 4b. Accordingly, it is desired to make the detector ring region 41 having the level by which a suppressed influence is obtainable.

PREFERRED EMBODIMENT 3

Figure 5:
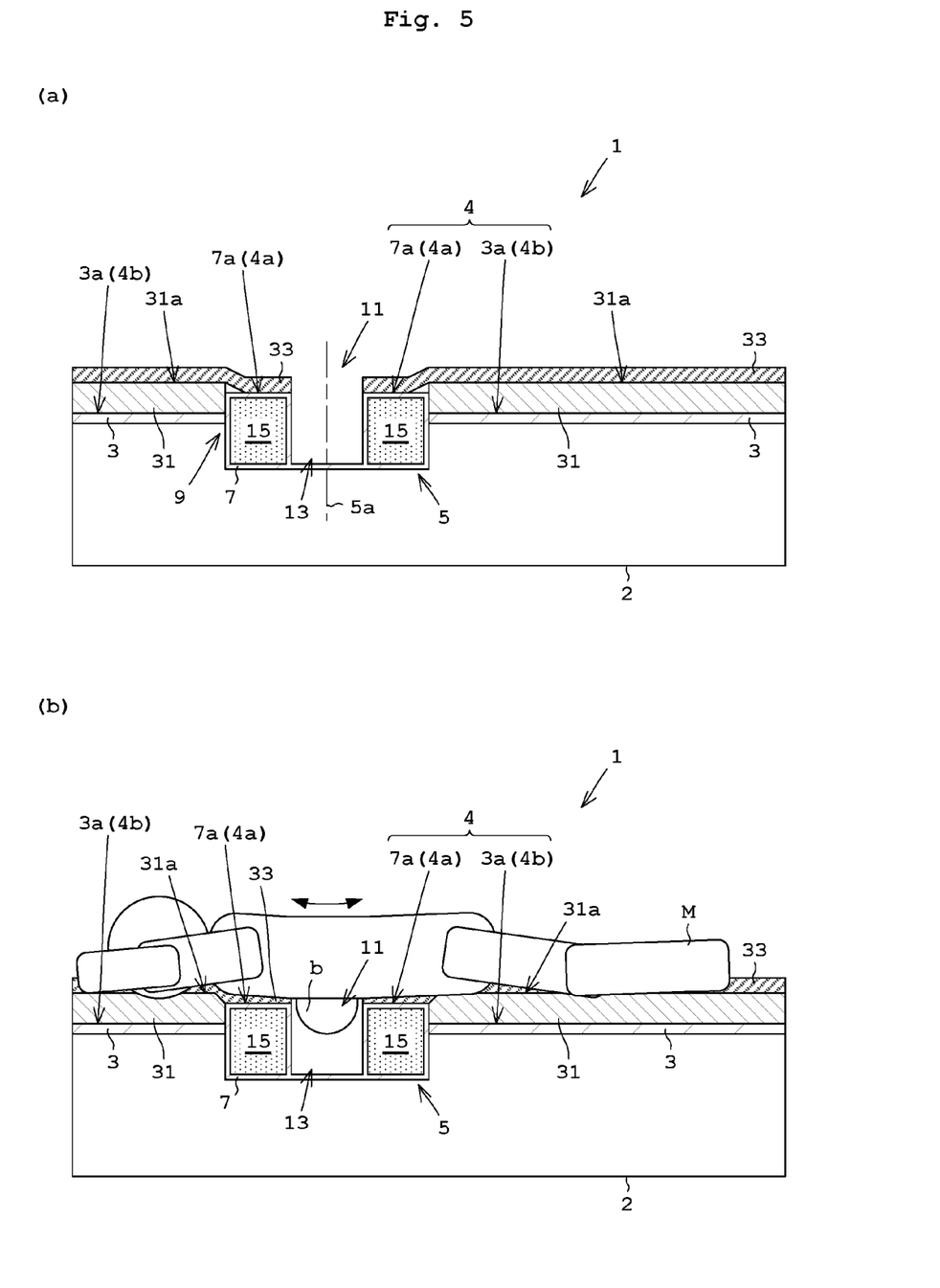
FIG. 5(a) is a vertical sectional view of a mammography PET apparatus according to Preferred Embodiment 3.
FIG. 5(b) illustrates the mammography PET apparatus of FIG. 5(a) with a subject placed therein.

The following describes Preferred Embodiment 3 of the present invention with reference to drawings. Here, description of the configuration common to that of Embodiment 1 is to be omitted. FIG. 5(a) is a vertical sectional view of a mammography PET apparatus according to the Preferred Embodiment 3, and FIG. 5(b) illustrates the mammography PET apparatus of FIG. 5(a) with a subject placed therein.

The Embodiment 1 mentioned above describes the relationship between the detector ring region 4a and the top face 31a of the lower-layer mat 31 such that the detector ring region 4a is equal in level to the top face 31a of the lower-layer mat 31. In contrast to this, as illustrated in FIGS. 5(a) and 5(b) of the present embodiment, the top face 31a of the lower-layer mat 31 is higher than the detector ring region 4a toward the subject M.

In the present embodiment, the detector ring region 4a is lower than the lower-layer mat 31. Accordingly, the torso of the subject M warps and naturally stretches, achieving more effective insertion of the breast b of the subject M into the field of view.

PREFERRED EMBODIMENT 4

Figure 6:
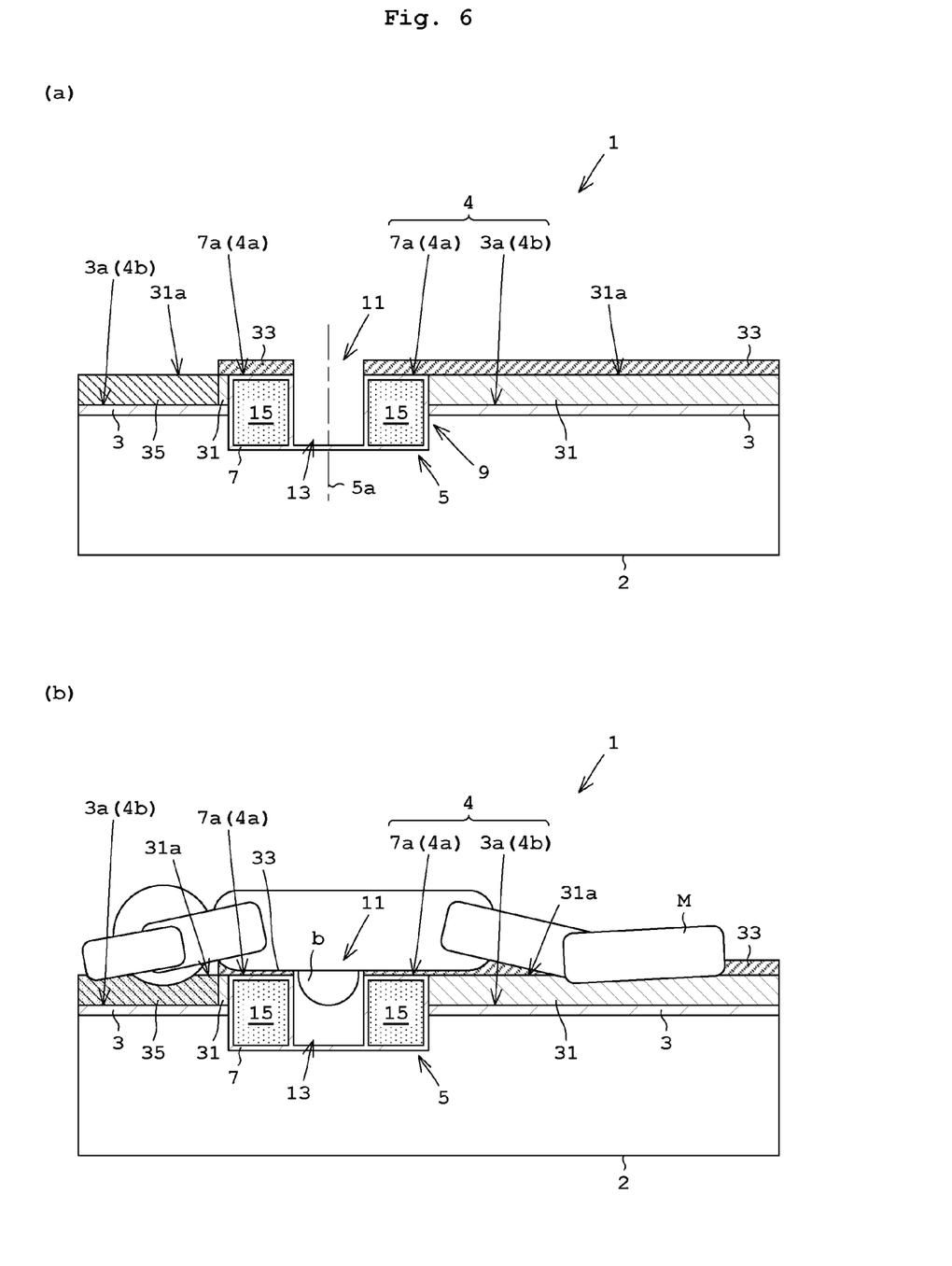
FIG. 6(a) is a vertical sectional view of a mammography PET apparatus according to Preferred Embodiment 4.
FIG. 6(b) illustrates the mammography PET apparatus of FIG. 6(a) with a subject placed therein.
Figure 7:
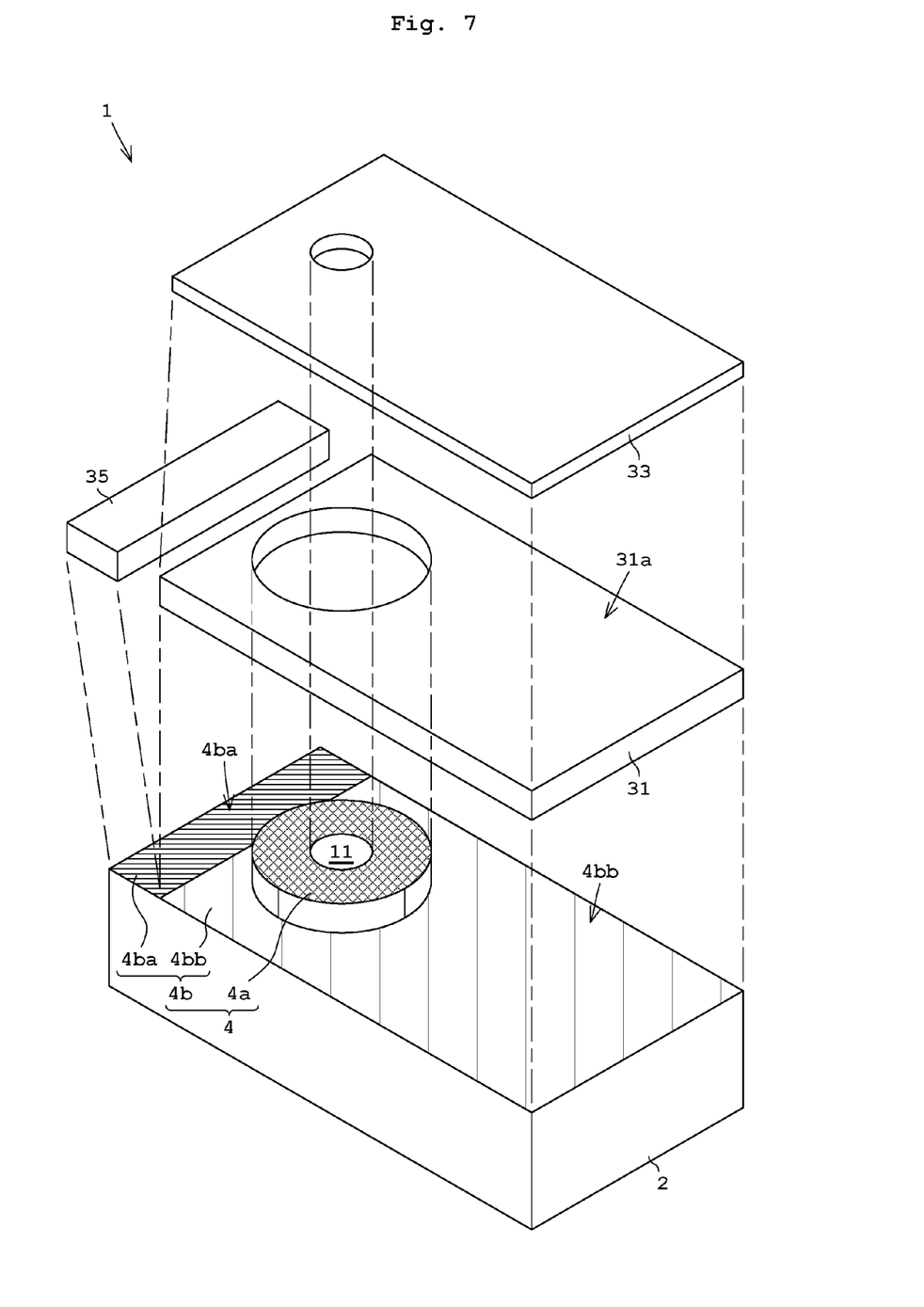
FIG. 7 is an exploded perspective view of the mammography PET apparatus according to the Preferred Embodiment 4.
Figure 8:
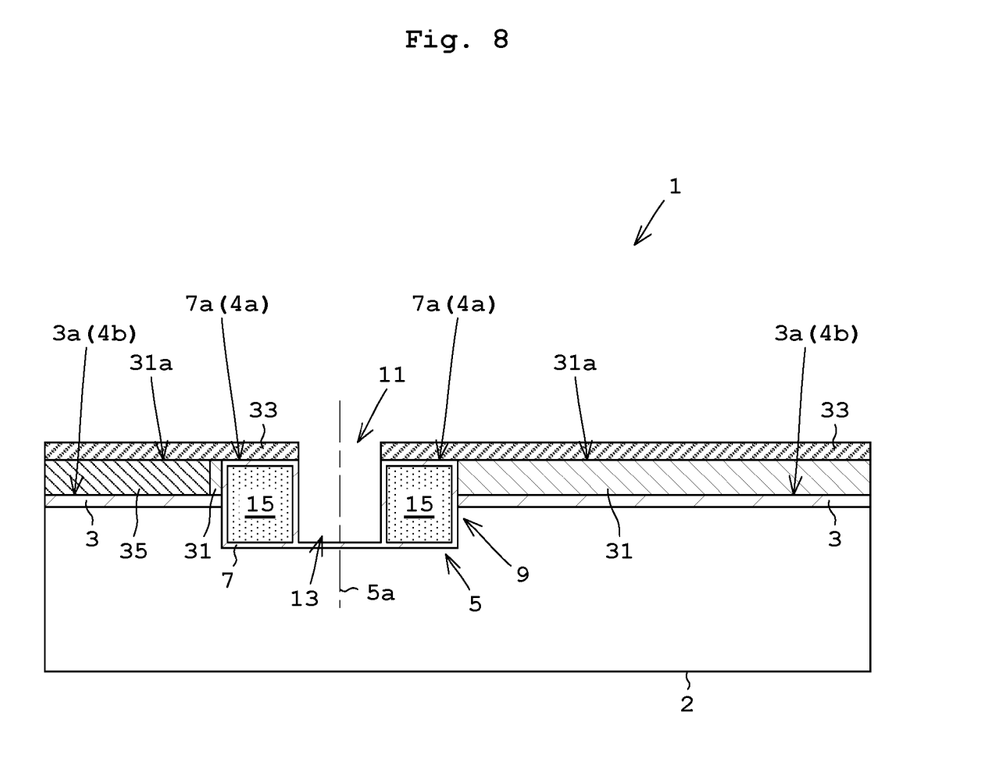
FIG. 8 is a vertical sectional view of a mammography PET apparatus according to one modification of the Preferred Embodiment 4.

The following describes Preferred Embodiment 4 of the present invention with reference to drawings. Here, description of the configuration common to that of Embodiments 1 to 3 is to be omitted. FIG. 6(a) is a vertical sectional view of a mammography PET apparatus according to the Preferred Embodiment 4, and FIG. 6(b) illustrates the mammography PET apparatus of FIG. 6(a) with a subject placed therein. FIG. 7 is an exploded perspective view of the mammography PET apparatus according to the Embodiment 4. FIG. 8 is a vertical sectional view of a mammography PET apparatus according to one modification of the Embodiment 4.

In the Embodiments 1 to 3 mentioned above, only the lower-layer mat 31 is disposed on the detector-outside region 4b. In contrast to this, as illustrated in FIGS. 6(a) and 6(b) of the present embodiment, instead of the lower-layer mat 31, a head mat 35 softer than the lower-layer mat 31 is disposed on a head region 4ba corresponding to the head of the subject M.

As illustrated in FIG. 3, the supporting face 4 includes the detector ring region 4a and the detector-outside region 4b. As illustrated in FIG. 7, the detector-outside region 4b is divided into the head region 4ba corresponding to the head of the subject M and a head-outside region 4bb other than the head region 4ba. Moreover, the lower-layer mat 31 is disposed on the head-outside region 4bb, and the head mat 35 softer than the lower-layer mat 31 is disposed on the head region 4ba.

The head mat 35 is, for example, formed by a material having the same property as that of the upper-layer mat 33. That is, the head mat 35 is formed by a sponge of the same hardness, of the same material such as urethane, and of the same type.

The upper-layer mat 33 is disposed on the detector ring region 4a and the lower-layer mat 31 in the same manner as that in the Embodiments 1 to 3. Moreover, as illustrated in FIG. 8, the upper-layer mat 33 may cover the head mat 35. That is, the upper-layer mat 33 is disposed on the detector ring region 4a, the lower-layer mat 31, and the head mat 35.

Since the head of subject M structurally projects forward from the chest wall, load is likely to be applied to the head when the subject M is pressed toward the detector ring 5. Consequently, the head causes prevention of the pressing. Then, the head mat 35 softer than the lower-layer mat 31 is disposed in the present embodiment, and the head of the subject M sinks more deeply in the head mat 35 than in the lower-layer mat 31 so as not to prevent the pressing.

The present invention is not limited to the foregoing examples, but may be modified as follows.

Figure 9:
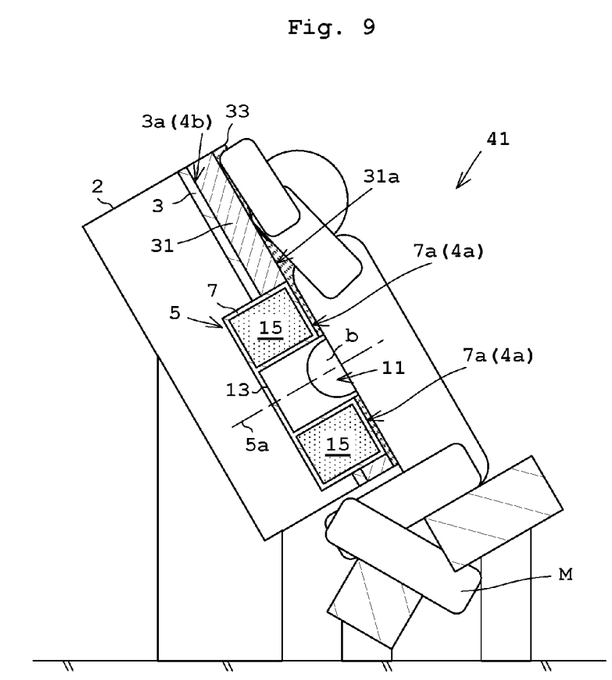
FIG. 9 is a vertical sectional view of the mammography PET apparatus according to the modification.

(1) In each of the embodiments mentioned above, the supporting face 4 is horizontal. However, the supporting face 4 may be inclined. Moreover, as illustrated in FIG. 9, the mammography PET apparatus 41 may have a configuration in which the subject M leans on the detector ring 5 while sitting on a chair (i.e., in a seated position). In such a case, the supporting face 4 (4a, 4b) of the supporting unit 2 is inclined. The detector ring 5 has a plurality of γ-ray detectors 15 arranged in a ring shape including a polygon shape about an axis 5a of the accommodating unit 13 perpendicular with respect to the supporting face 4.

(2) In each of the embodiments and the modification (1) mentioned above, the supporting face 4 includes the top board supporting face 3a of the top board 3 and the case supporting face 7a of the case 7. In contrast to this, the case supporting face 7a may include the top board 3. That is, the top board 3 may be processed to have irregularities, and the detector ring region 4a and the detector-outside region 4b (i.e., the supporting face 4) may be formed by only the top board 3. In such a case, the detector ring 5 may or may not have the case 7.

Figure 10:
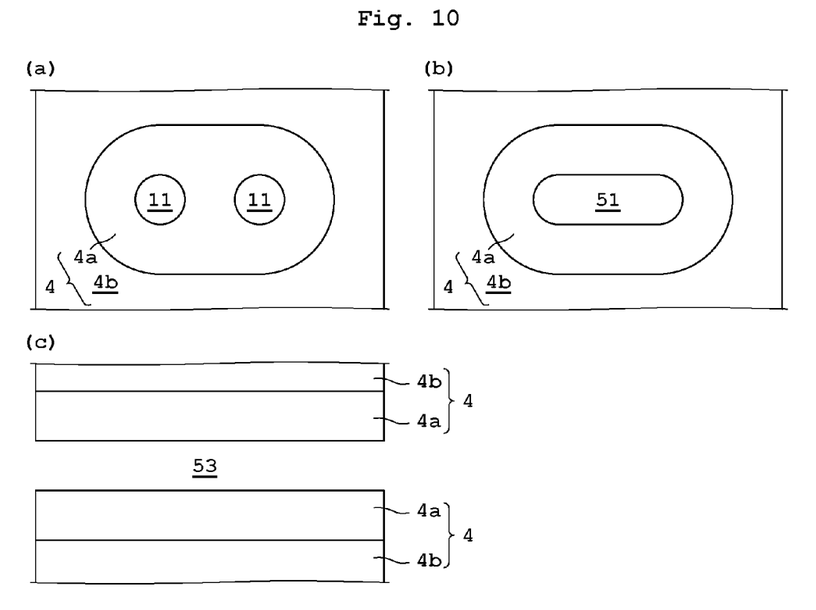

(3) In each of the embodiments and the modifications mentioned above, the supporting face 4 includes one opening 11 into which one breast b of the subject M is inserted. However, this is not limitative. FIG. 10 illustrates a condition without the lower-layer mat 31, the upper-layer mat 33, and the like. For instance, as illustrated in FIG. 10(a), the supporting face 4 may include two openings 11. Moreover, as illustrated in FIG. 10(b), the supporting face 4 may include one opening 51 into which two breasts b of the subject M are inserted. Moreover, as illustrated in FIG. 10(c), the opening 53 may be formed by a clearance between separated supporting faces 4. Moreover, the detector ring 5 that captures one breast b may be movable, and may capture every one of the two breasts b inserted into the openings 11, 51, and 53 of FIGS. 10(a) to 10(c), respectively. Moreover, the detector ring 5 may have a size sufficient to surround the two breasts b.

(4) Each of the embodiments and the modifications describes the mammography PET apparatus that administers the radiopharmaceutical containing positron-emitting radionuclide to the subject, and detects two γ-rays emitted from the subject M. However, this is not limitative. That is, a SPECT apparatus is applicable that administers single photon emission nuclide to the subject M, and detects one γ-ray emitted from the subject M.

(5) Each of the embodiments and the modifications describes the mammography PET apparatus taking the breast of the subject for the capturing target site as one example of the nuclear medicine diagnosis apparatus. Alternatively, a PET apparatus taking another site for the capturing target site is applicable.

REFERENCE SIGN LIST 1, 41 . . . mammography PET apparatus
2 . . . supporting unit
3 . . . top board
3a . . . top board supporting face
4 . . . supporting face
4a . . . detector ring region
4b . . . detector-outside region
4ba . . . head region
4bb . . . head-outside region
5 . . . detector ring
7 . . . case
7a . . . case supporting face
11, 51, 53 . . . opening
23 . . . main controller
31 . . . lower-layer mat
33 . . . upper-layer mat
35 . . . head mat

The invention claimed is:

1. A nuclear medicine diagnosis apparatus, comprising:
a supporting unit that supports a subject;
an opening formed on a supporting face of the supporting unit into which a capturing target site as a projection part of the subject is inserted; and
a detector ring opposite to the subject across the supporting face of the supporting unit and including a plurality of detectors in a ring-shape arrangement for detecting radiation emitted from the capturing target site inserted into the opening, wherein
the supporting face includes a detector ring region corresponding to the arrangement of the detector ring, and a detector-outside region as to an outside area of the detector ring region,
the detector ring region is higher than the detector-outside region,
an elastic lower-layer mat is disposed on the detector-outside region, and
an upper-layer mat softer than the lower-layer mat is disposed on the detector ring region and the lower-layer mat across a boundary between the detector ring region and the lower-layer mat.

2. The nuclear medicine diagnosis apparatus according to claim 1, wherein
the detector-outside region is divided into a head region corresponding to the head of the subject, and a head-outside region other than the head region, and
the lower-layer mat is disposed on the head-outside region, and a head mat softer than the lower-layer mat is disposed on the head region.

3. The nuclear medicine diagnosis apparatus according to claim 1, wherein
the detector ring region is equal in level to a top face of the lower-layer mat.

4. The nuclear medicine diagnosis apparatus according to claim 1, wherein
the detector ring region is higher than a top face of the lower-layer mat toward the subject.

5. The nuclear medicine diagnosis apparatus according to claim 1, wherein
a top face of the lower-layer mat is higher than the detector ring region toward the subject.

* * * * *